(12) United States Patent
Hyun

(10) Patent No.: US 9,265,699 B2
(45) Date of Patent: Feb. 23, 2016

(54) GRAVITY FEEDING DEVICE

(75) Inventor: Dongchul D. Hyun, Brea, CA (US)

(73) Assignee: MEDELA HOLDING AG, Baar (CH)

( * ) Notice: Subject to any disclaimer, the term of this patent is extended or adjusted under 35 U.S.C. 154(b) by 1334 days.

(21) Appl. No.: 12/577,419

(22) Filed: Oct. 12, 2009

(65) Prior Publication Data

US 2011/0087193 A1    Apr. 14, 2011

(51) Int. Cl.
| | |
|---|---|
| *A61J 9/04* | (2006.01) |
| *A61J 9/00* | (2006.01) |
| *A61J 1/14* | (2006.01) |
| *A61M 3/02* | (2006.01) |
| *A61J 15/00* | (2006.01) |
| *A61M 39/08* | (2006.01) |

(52) U.S. Cl.
CPC *A61J 9/00* (2013.01); *A61J 1/2075* (2015.05); *A61J 1/1412* (2013.01); *A61J 1/2068* (2015.05); *A61J 9/04* (2013.01); *A61J 15/0026* (2013.01); *A61M 3/0241* (2013.01); *A61M 2039/085* (2013.01); *A61M 2202/0482* (2013.01)

(58) Field of Classification Search
CPC ............ A61M 5/1411; A61M 3/0241; A61M 2202/0482; A61M 2005/16863; A61M 2005/1686; A61M 2005/16872; A61M 2205/7554; A61M 2205/7563; A61M 2039/085; A61J 15/00; A61J 15/0026; A61J 7/0046; A61J 1/1462; A61J 1/145; A61J 1/1412; A61J 9/00; A61J 9/04; A61J 9/08; A61J 9/06; A61J 1/2068; A61J 1/2075
USPC ............. 604/77, 80, 262, 514, 516, 251–253, 604/257, 910, 403
See application file for complete search history.

(56) References Cited

U.S. PATENT DOCUMENTS

| | | | |
|---|---|---|---|
| 2,176,057 A | 10/1939 | Burkardt | |
| 2,228,435 A | 1/1941 | Binon | |
| 2,600,978 A | 6/1952 | Demarco, Jr. | |
| 2,969,064 A | 1/1961 | Metz | |
| 3,149,758 A | 9/1964 | Bush et al. | |
| 3,153,415 A | 10/1964 | Sheridan | |
| 3,165,241 A | 1/1965 | Curry | |
| 3,645,262 A | 2/1972 | Harrigan | |
| 3,672,052 A | 6/1972 | Mason | |
| 4,687,473 A * | 8/1987 | Raines .......................... | 604/251 |
| 4,753,639 A * | 6/1988 | Iwatschenko ................. | 604/246 |
| D315,096 S | 3/1991 | Rocchio | |
| 5,049,127 A | 9/1991 | Yen Tseng | |
| 5,078,699 A * | 1/1992 | Haber et al. .................. | 604/250 |
| 5,501,348 A | 3/1996 | Takeuchi | |
| 6,120,528 A | 9/2000 | Link et al. | |
| 6,129,703 A | 10/2000 | Beneke | |
| 6,966,904 B2 | 11/2005 | Ruth et al. | |
| 7,320,678 B2 | 1/2008 | Ruth et al. | |

(Continued)

*Primary Examiner* — Bhisma Mehta
*Assistant Examiner* — Laura Schell
(74) *Attorney, Agent, or Firm* — Stetina Brunda Garred & Brucker

(57) ABSTRACT

A gravity fed infant feeding device is disclosed. The gravity feeding device may have a cover with a through hole that allows liquid nutrients within the infant feeding device to be fed to an infant by way of gravity. If the infant feeding device clogs up, then either an integrated pump or a separate pump may be applied to the infant feeding device to increase pressure and push out the clog from the system. the through hole may be covered with a hydrophobic filter to allow air to pass there through and allow the feeding of the infant by way of gravity yet liquid nutrients within the infant feeding device cannot escape or be contaminated during use.

2 Claims, 4 Drawing Sheets

(56) References Cited

U.S. PATENT DOCUMENTS

2004/0173556 A1* 9/2004 Smolko et al. .............. 215/11.5
2008/0103475 A1* 5/2008 Hendricks .................... 604/403
2010/0038336 A1* 2/2010 Kheradvar et al. .......... 215/11.5

* cited by examiner

GRAVITY FEEDING DEVICE

CROSS-REFERENCE TO RELATED APPLICATIONS

Not Applicable

STATEMENT RE: FEDERALLY SPONSORED RESEARCH/DEVELOPMENT

Not Applicable

BACKGROUND

The present invention relates to a gravity feeding device for feeding liquid nutrients to a hospitalized infant.

Two common methods of feeding breast milk or liquid formula to a hospitalized infant exist. One method uses a syringe pump to provide a continuous flow of milk by mechanically depressing a plunger of a syringe filled with liquid nutrients (e.g., breast milk, liquid infant formula, etc.). This is a clumsy process since the plunger must be removed to fill the syringe with liquid nutrients. The medical professional must then hold the bottle of liquid nutrients and the barrel to pour the liquid nutrients into the barrel while maintaining sterility of the plunger. Also, the liquid nutrients might spill over and contaminate surrounding areas.

The second method consists of removing the plunger from the barrel or cylindrical pipe portion of the syringe. The liquid nutrients are transferred into the barrel which is manually held uncovered to allow the liquid nutrients to flow out of a barrel by gravity until the feeding process is over. Since the barrel is uncovered, the possibility of spillage or contamination is present. During feeding, liquid nutrients may clog a narrow outlet of the syringe. To unclog the narrow outlet of the syringe, the plunger is reinserted into the barrel to increase air pressure above the liquid. This takes time and further increases the possibility of spillage or contamination.

Accordingly, there is a need in the art for an improved feeding device for an infant.

BRIEF SUMMARY

The infant feeding device disclosed herein addresses the needs discussed above, discussed below and those that are known in the art.

The infant feeding device may have a gravity feeding container which defines a fluid chamber. Liquid nutrients may be poured into the fluid chamber for storage and subsequent delivery to an infant during operation. The infant feeding device may have a cover with a through hole to allow air molecules to enter the fluid chamber during operation. The addition of air molecules within the fluid chamber prevents formation of a vacuum in the fluid chamber that might stop the flow of liquid nutrients out of an enteral feeding tube connected to the infant feeding device since gravity might not be able to overcome the vacuum pressure within the fluid chamber. A hydrophobic filter may be disposed over the through hole to allow the air molecules to pass into the fluid chamber yet prevent the liquid nutrients from spilling during accidental droppage or inversion of the infant feeding device or to prevent contaminants from entering into the fluid chamber.

When the system is clogged, a pump may increase pressure within the fluid chamber to push the particulate clogging the system out of the infant feeding device or the enteral feeding tube. More particularly, the cover may have an integrated pump or diaphragm that is traversable between a retracted position and a depressed position. The through hole is formed in the diaphragm such that an operator simultaneously closes the through hole with his/her finger and continues to push downward to traverse the diaphragm from the retracted position to the depressed position. This seals and also increases pressure within the fluid chamber to assist in clearing any clogs. Alternatively, the cover may have a through hole which is sized and configured to provide an airtight seal with a tapered stem of a standard aspiration bulb. To clear the infant feeding device of any clogs, the tapered stem of the aspiration bulb is inserted into the through hole so as to form an airtight seal of air between. The operator squeezes a bulb portion of the aspiration bulb to increase pressure within the fluid chamber and push out the particulate clogging the system.

In an embodiment, an infant feeding device may comprise a body defining a fluid chamber for holding liquid nutrients, a bottom output end portion connectable to an enteral feeding tube for flowing the liquid nutrients to an infant, and an upper opening for introducing air molecules into the fluid chamber to allow the liquid nutrients to flow out of the bottom output end portion by way of gravity wherein the upper opening is sized and configured to form an airtight seal with a tapered stem portion of an aspiration bulb for unclogging the reduced size throat or the enteral feeding tube.

The upper opening may be the only opening to allow the aspiration bulb to both seal the fluid chamber and increase pressure within the fluid chamber for unclogging the bottom output end portion or the enteral feeding tube.

The body may comprise a container and a cover disposed at an upper end portion of the container. The upper opening may be formed in the cover. A tether may be attached to the container and the cover for retaining the cover to the container when the cover is dislodged from the container. A sealing wall may extend from an inner peripheral edge of the upper opening. The sealing wall may have a frusto conical configuration.

The device may further comprise a retainer and a hydrophobic filter. The retainer may be attached to the sealing wall and the hydrophobic filter may be attached to the retainer. The retainer may have a frusto conical wall with a proximal portion attached to the sealing wall and a support platform formed at a distal portion. The hydrophobic filter may be attached to the support platform. The hydrophobic filter may be mounted within the body between the fluid chamber of the container and the upper opening for allowing air to pass between the fluid chamber and the environment and preventing fluid from passing between the fluid chamber and the environment.

A twist lock receptacle having a non standard luer fitting may be formed at the bottom end portion.

In another embodiment, an infant feeding device may comprise a body defining a fluid chamber for holding liquid nutrients. The body may have a bottom output end portion connectable to an enteral feeding tube for flowing the liquid nutrients out of the fluid chamber and an upper opening for introducing air molecules into the fluid chamber so that the liquid nutrient can flow out of the reduced size throat by way of gravity. The upper portion of the body may have a moveable diaphragm for unclogging the bottom output end portion or the enteral feeding tube by depressing the diaphragm.

The body may comprise a container and a cover. The container may be generally rigid and having the bottom output end portion. The container may have an open top. The cover may be attached to the open top of the container wherein the moveable diaphragm is formed in the cover and the upper opening is formed in the diaphragm so that a finger can both seal the fluid chamber and increase pressure within the fluid chamber for unclogging the bottom output end portion or the enteral feeding tube.

The diaphragm may be biased toward a retracted position and traversable to a depressed position for increasing pressure within the fluid chamber to unclog the bottom output end portion or the enteral feeding tube.

The device may further comprise a retainer with a hydrophobic filter attached to the retainer. The retainer may be attached to the cover and aligned to the upper opening so that the hydrophobic filter is disposed between the environment and the fluid chamber to allow air to pass through the upper opening and to prevent liquid from passing through the upper opening.

In another embodiment, a method of operating a feeding device for an infant is disclosed. The method may comprise the steps of filling a fluid chamber of the infant feeding device with liquid nutrients; orienting a reduced size throat of the infant feeding device to a lowered position to discharge the liquid nutrients from the fluid chamber by way of gravity; discharging the liquid nutrients out of the reduced size throat by way of gravity by providing air communication between the fluid chamber and the environment through a vent formed above a liquid level of the liquid nutrients disposed within the fluid chamber; when the reduced size throat is clogged, closing the vent by hand and increasing pressure within the fluid chamber to unclog the reduced size throat; removing the hand from the vent to open the vent; and resuming the discharging step.

The closing step may comprise the step of plugging the vent with a finger of a person. Also, the increasing pressure step may comprise the step of pushing the closed vent toward the fluid chamber to increase pressure within the fluid chamber.

The vent may be formed in a diaphragm traversable between a depressed position and a retracted position. The pushing step may comprise the step of pushing the diaphragm toward the fluid chamber.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Figure 1:
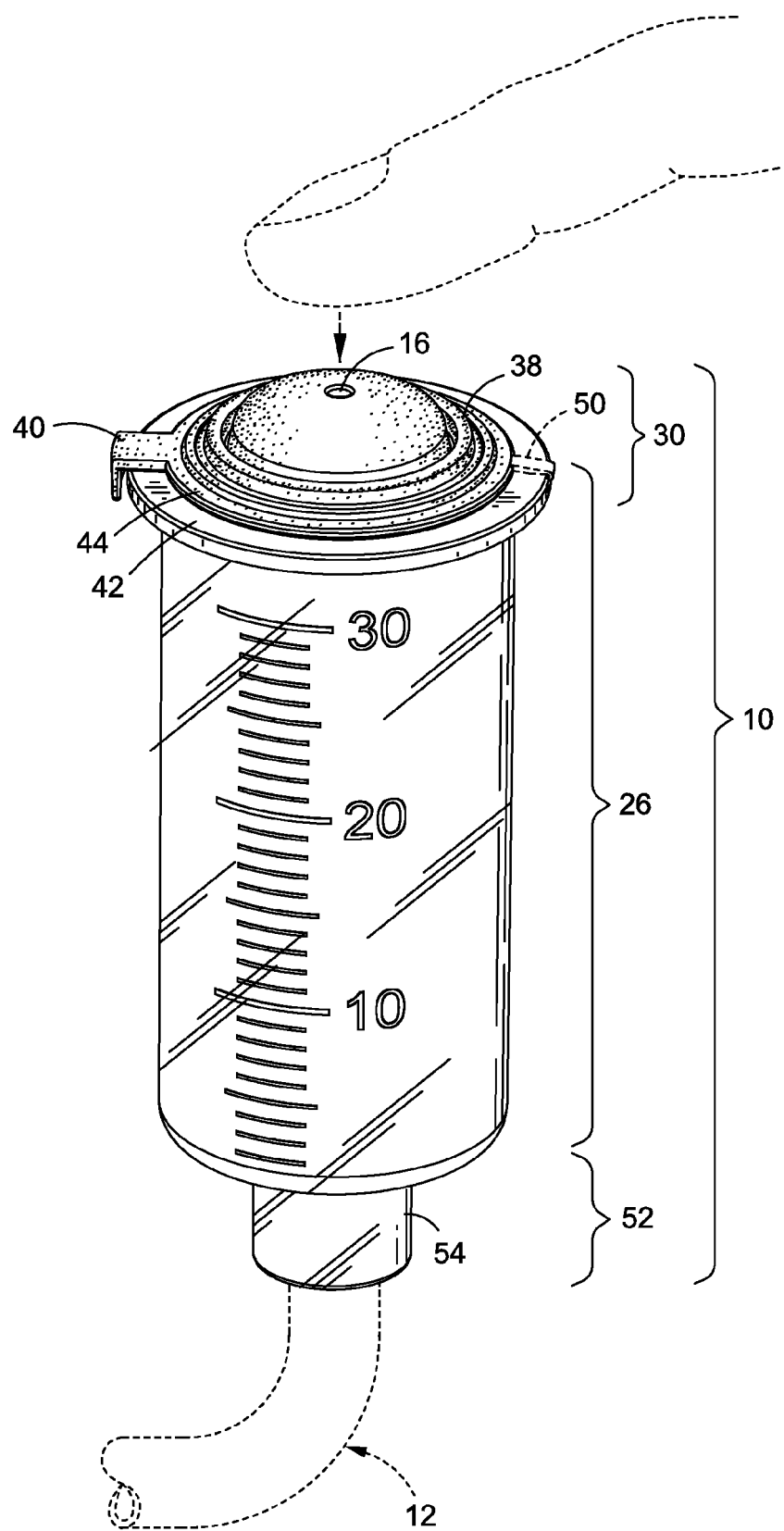
FIG. 1 is a perspective view of a first embodiment of an infant feeding device.

Referring now to FIG. 1, an infant feeding device 10 is shown. The infant feeding device 10 may be removably connected to an enteral feeding tube 12. Liquid nutrients 14 may be disposed within the infant feeding device 10. A through hole 16 is formed at a position above the upper surface 18 of the liquid nutrients 14, and preferably, in a cover 30. By way of gravity, the liquid nutrients 14 are forced through the enteral feeding tube 12 to feed an infant. As the liquid nutrients 14 are flowed through the enteral feeding tube 12, air is introduced into the infant feeding device 10 by way of the through hole 16. The through hole 16 allows additional air molecules to enter the infant feeding device 10 such that a vacuum does not form within the infant feeding device 10. A vacuum may prevent the gravity fed flow of liquid nutrients 14 through the enteral feeding tube 12. In the event that the enteral feeding tube 12 or a reduced size throat 20 of the infant feeding device 10 is clogged, an operator may cover or plug the through hole 16 and push down on a diaphragm 22 (see dash lines in FIG. 2) to increase the pressure within the infant feeding device 10 and push out any particulate within the enteral feeding tube 12 or the reduced size throat 20 clogging the system. After the clog is cleared, the user releases the diaphragm 22 which may spring back up to its biased retracted position (see solid lines in FIG. 2). The liquid nutrients 14 may now flow out of the enteral feeding tube 12 by way of gravity since the through hole 16 is not blocked. Also, when the enteral feeding tube 12 or the reduced size throat 20 is clogged again, the user may quickly and easily repeat the process described above. The infant feeding device 10 provides for quick and easy clearance of clogs.

Figure 3:
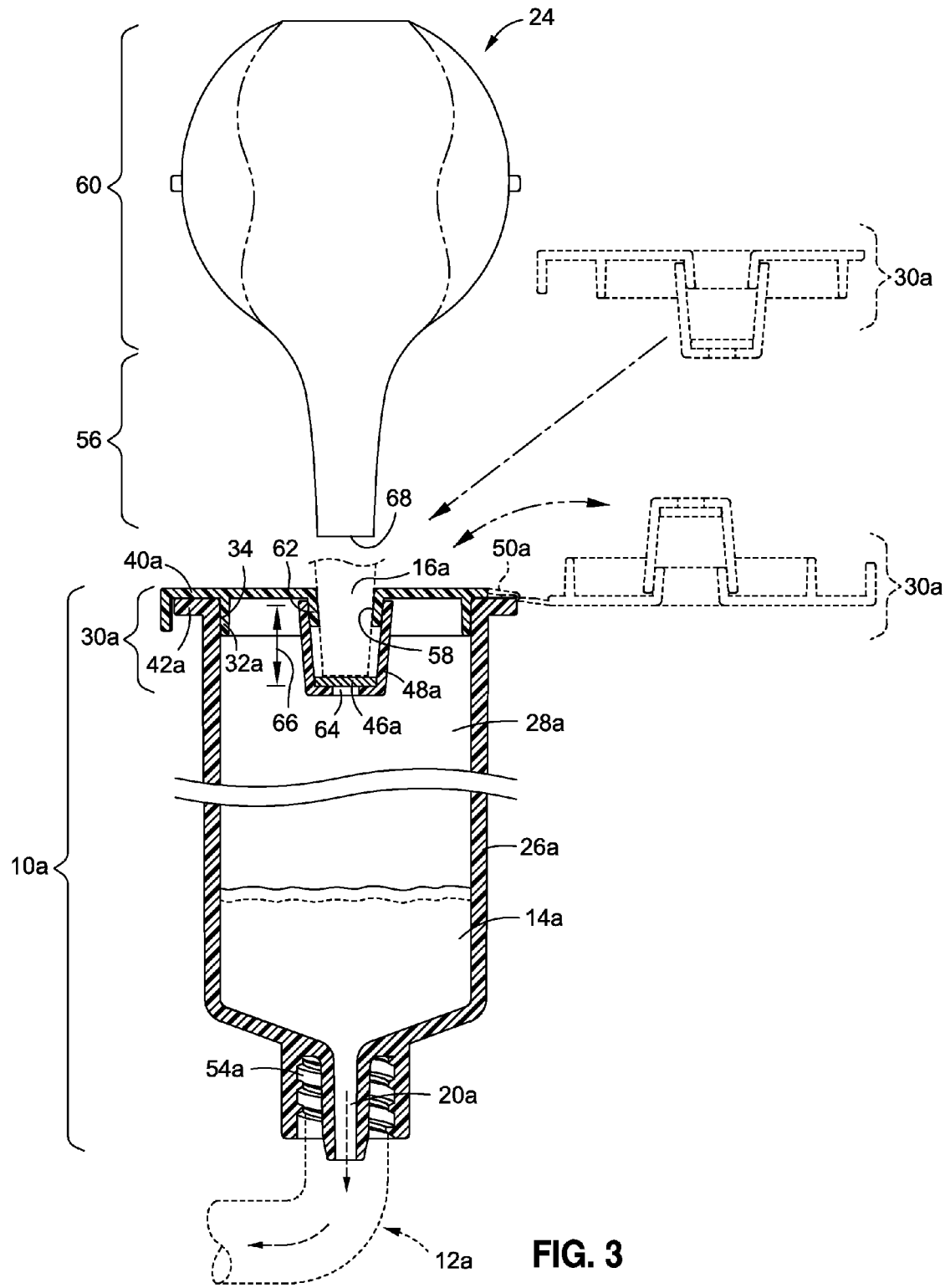
FIG. 3 is a cross sectional view of a second embodiment of an infant feeding device.

Alternatively, with respect to a second embodiment shown in FIG. 3, an aspiration bulb 24 may be inserted into a through hole 16a to clear a clog within the reduced size throat 20a of an infant feeding device 10a or the enteral feeding tube 12a to increase a pressure within the infant feeding device 10a and unclog any clogs within the reduced size throat 20a or enteral feeding tube 12a. After the clog is cleared, the aspiration bulb 24 may be removed and feeding may continue. The infant feeding device 10a also provides for quick and easy clearance of the clog.

More particularly, referring back to FIGS. 1 and 2, the infant feeding device 10 may comprise a gravity feeding container 26 which may be fabricated from a generally rigid material to resist bulging of the gravity feeding container 26 when positive pressure is applied within the infant feeding device 10 to clear any clogs within the enteral feeding tube 12 or reduced size throat 20. The gravity feeding container 26 may have a generally cylindrical configuration with an open top. Liquid nutrients 14 may be poured into the gravity feeding container 26 by holding the gravity feeding container 26 in an upright position while pouring the liquid nutrients 14 into the gravity feeding container 26 which defines a fluid chamber 28. Once the liquid nutrients 14 are disposed within the fluid chamber 28, a cover 30 may close the open top of the gravity feeding container 26. The cover 30 may have an inner peripheral lip 32 (see FIG. 2) that may be seated to an upper inner peripheral surface 34 of the gravity feeding container 26. An airtight seal is formed between the inner peripheral lip 32 of the cover 30 and the upper inner peripheral surface 34 of the gravity feeding container 26. The through hole 16 may be formed through the cover 30 and may provide the only means of air communication between the fluid chamber 28 and the environment 36 during use. As the liquid nutrients 14 are flowed through the enteral feeding tube 12 by gravity, air molecules are introduced into the fluid chamber 28 by way of the through hole 16 to prevent creation of a vacuum within the fluid chamber 28 that might prevent the flow of liquid nutrients 14 through the enteral feeding tube 12.

As the liquid nutrients 14 are flowed out of the reduced size throat 20 and the enteral feeding tube 12, at certain times, the same 20, 12 may be clogged thereby preventing flow of liquid nutrients 14 through the enteral feeding tube 12 and ultimately to the infant. To clear the clog, the through hole 16 may be plugged and the diaphragm 22 pushed downwardly to increase pressure within the fluid chamber 28. The increased pressure will urge any particulate clogged within the reduced size throat 20 or enteral feeding tube 12 out and unclog the system. More particularly, an operator's finger may cover the through hole 16 as shown in FIG. 1 and push the diaphragm 22 toward the fluid chamber 28, as shown by the dash lines in FIG. 1. Convolutes 38 allow for the diaphragm 22 to be pushed toward the fluid chamber 28. The convolutes 38 bend and straighten out as shown by the hidden lines in FIG. 2. Depressing the diaphragm 22 toward the fluid chamber 28 displaces the air within the fluid chamber 28 to increase the pressure within the fluid chamber 28. The increased pressure correspondingly increases pressure of the liquid nutrients 14 within the reduced size throat 20 and the enteral feeding tube 12 thereby pushing the particulate clogging the system out of the system. A small amount of liquid nutrients 14 is pushed out of the infant feeding device 10 as shown by the lowered upper surface of the liquid nutrients 14 shown in dash lines. Upon removing the finger of the operator from the diaphragm 22, the convolutes 38 urge the diaphragm 22 back up into its normal position as shown by the solid lines in FIG. 2. This resets the infant feeding device 10 such that the operator can unclog any future clogs within the system.

The cover 30 may additionally have an opening tab 40. When the cover 30 is mounted to the gravity feeding container 26, there may be a friction fit between the inner periphery lip 32 of the cover 30 and the upper inner peripheral surface 34 of the gravity feeding container 26. To help dislodge the cover 30 from the gravity feeding container 26, a user may push up or pull up on the opening tab 40 to dislodge the cover 30 from the gravity feeding container 26. The gravity feeding container 26 may have a flange 42 which extends outwardly from the upper end of the gravity feeding container 26. The cover 30 may additionally have a mating flange 44 which limits insertion of the inner peripheral lip 32 of the cover 30 into the fluid chamber 28 of the gravity feeding container 26. The opening tab 40 may extend beyond the outer periphery of the flange 42 of the gravity feeding container 26 and be turned downwardly, as shown in FIG. 1. The user may pull upward or push upward on the opening tab 40 to dislodge the cover 30 from the gravity feeding container 26.

A hydrophobic filter 46 may be attached to the diaphragm 22 to cover the through hole 16. The hydrophobic filter 46 allows air molecules to pass through the through hole 16 and into the fluid chamber 28 yet prevents liquid nutrients 14 from spilling out of the through hole 16 in the event that the infant feeding device 10 is accidentally dropped or inverted. There is less of an opportunity for contamination or spillage. The hydrophobic filter 46 may be secured over the through hole 16 by a retainer 48. The retainer 48 may be adhered, sonically welded, or otherwise attached to the diaphragm 22 via methods known in the art or developed in the future. Likewise, the hydrophobic filter 46 may be disposed between the retainer 48 and the diaphragm 22 and secured to the retainer 48 in a similar fashion.

The convolutes 38 may have a thinner cross section compared to the diaphragm 22 and the inner peripheral lip 32 to allow bending and straightening of the convolutes 38. This allows the diaphragm 22 to be pushed downwardly as shown by the hidden lines in FIG. 2 even through the other components (e.g., diaphragm 22 or lip 32) are generally rigid. The gravity feeding container 26 and the cover 30 may be molded in one step.

Figure 2:
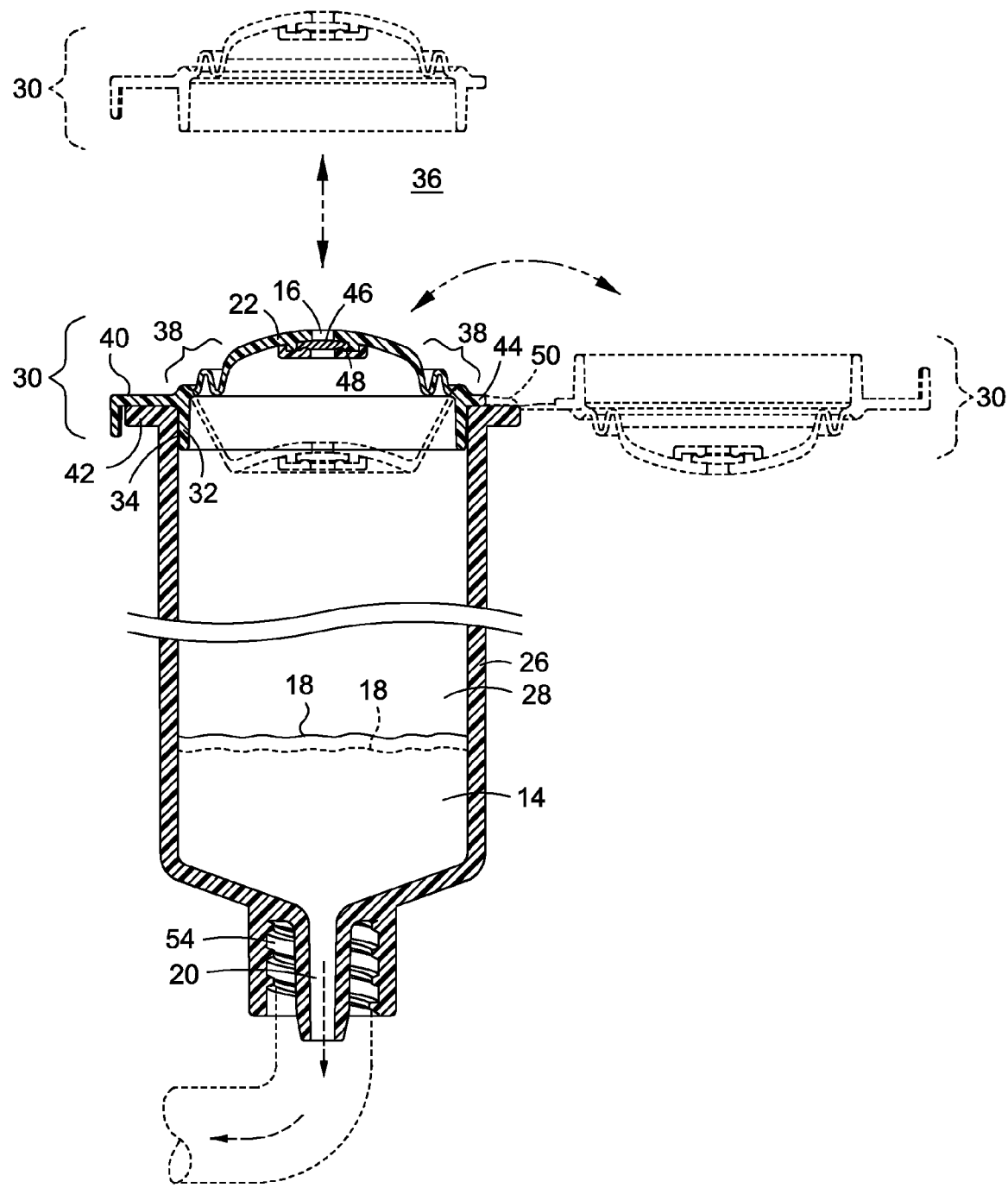
FIG. 2 is a cross sectional view of the infant feeding device shown in FIG. 1.

Optionally, the infant feeding device 10 may have a tether 50 that retains the cover 30 and the gravity feeding container 26 together when the cover 30 is dislodged from the gravity feeding container 26. As shown in FIG. 2, the cover 30 shown in hidden lines on the right side of the gravity feeding container 26 is connected to the gravity feeding container 26 such that the cover 30 cannot be lost.

The lower end portion 52 of the gravity feeding container 26 may have a receptacle 54 which connects to the enteral feeding tube 12. The receptacle 54 may be a non-standard twist lock receptacle which is sized to not allow connection of standard luer fitting devices. The enteral feeding tube 12 may have a corresponding non-standard twist lock receptacle for mating with the receptacle 54 of the gravity feeding container 26. In this manner, only enteral feeding tubes can connect to the infant feeding device 10 and the corresponding enteral feeding tube 12 cannot connect to a standard syringe. This reduces the possibility or opportunity of misconnecting the feeding tube 12 which is a serious problem. By way of example and not limitation, the non standard twist lock receptacle 54 may have a larger diameter and/or a different taper angle compared to standard luer fittings.

Referring now to FIG. 3, a second embodiment of the infant feeding device 10a is shown. The infant feeding device 10a comprises the gravity feeding container 26a and a cover 30a. The cover 30a is operative to close the open top of the gravity feeding container 26a during use. The cover 30a may have a through hole 16a to allow air molecules to enter the fluid chamber 28a while liquid nutrients 14a are flowed through an enteral feeding tube 12a. The through hole 16a prevents a vacuum forming within the fluid chamber 28a which may prevent the flow of liquid nutrients 14 through the enteral feeding tube 12a. The infant feeding device 10a may work in conjunction with a standard aspiration bulb 24. The standard aspiration bulb 24 has a bulbous hollow area 60 connected to a tapered stem 56. The tapered stem 56 may be inserted into the through hole 16a and seal against an inner periphery 58 of the through hole 16a (i.e., against an internal tapered conical surface of the upper opening). Once the tapered stem 56 of the aspiration bulb 24 is inserted into the through hole 16a and sealed against the inner periphery 58 of the through hole 16a, then the bulb 60 may be squeezed (see dash lines of bulb 24) to supply positive pressure to the fluid chamber 28a. This positive pressure will urge the liquid nutrients 14a through the reduced size throat 20a and the enteral feeding tube 12a in the event that a particulate is clogging the system. To further aid in sealing the tapered stem 56 of the aspiration bulb 24 to the inner periphery 58 of the through hole 16a, the through hole 16a may further be defined by a frusto conical wall 62. The frusto conical wall 62 may be tapered at the same angle as compared to the tapered stem 56. This allows a greater surface area of the tapered stem 56 to contact and seal with the frosto conical wall 62. The frusto conical wall 62 may extend inwardly toward the fluid chamber 28a when the cover 30a is mounted to the gravity feeding container 26a.

The cover 30a may have an inner peripheral lip 32a which sealingly engages the upper inner peripheral surface 34 of the gravity feeding container 26a similar to the infant feeding device 10 described above.

A hydrophobic filter 46a may be interposed between the fluid chamber 28 and the through hole 16a such that during use air molecules can enter the fluid chamber 28 by way of the through hole 16a but liquid nutrients cannot spill out of the through hole 16a. More particularly, the hydrophobic filter 46a may be mounted to a retainer 48a. The retainer 48a may have a deep well cup configuration. At the bottom of the retainer 48a, a hole 64 may be formed which is covered by the hydrophobic filter 46a. The hydrophobic filter 46a may be attached to the bottom of the retainer 48a. The retainer 48a may have a depth 66 such that the tapered stem 56 of the aspiration bulb 24 may be inserted through the through hole 16a and a distal end 68 of the aspiration bulb 24 preferably does not contact the hydrophobic filter 46a when the tapered stem 56 is fully inserted into the through hole 16a.

Similar to the infant feeding device 10 described above, the infant feeding device 10a shown in FIG. 3 may have an opening tab 40a, flange 42a, tether 50a and receptacle 54a.

In use, the infant feeding device 10, 10a may be useful for feeding an infant. An enteral feeding tube 12, 12a may have a fitting that can only be connected to a specially designed receptacle 54, 54a. In this manner, the enteral feeding tube 12, 12a cannot be connected to a device other than the infant feeding device 10, 10a. Also, other types of non-feeding tubes cannot be attached to the infant feeding device 10, 10a. The cover 30, 30a may be dislodged from the gravity feeding container 26, 26a by pushing upward or pulling upward on the opening tab 40, 40a. The gravity feeding container 26, 26a has an open top which allows a person to pour in liquid nutrients 14 (e.g., breast milk, liquid formula, etc.) into the fluid chamber 28 of the gravity feeding container 26. The cover 30, 30a may be secured to the gravity feeding container 26, 26a by way of a tether 50, 50a to mitigate loss of the cover 30, 30a. Once the liquid nutrients 14, 14a are disposed within the fluid chamber 28, 28a, the cover 30, 30a is reattached to the gravity feeding container 26, 26a to close the open top of the gravity feeding container 26, 26a. The gravity feeding container 26, 26a is placed in an upright position such that the cover 30, 30a is above a reduced size throat 20, 20a. The cover 30, 30a may have a through hole 16, 16a which prevents formation of a vacuum within the fluid chamber 28 of the gravity feeding container 26 and allows the liquid nutrients 14 to flow out of the reduced size throat 20, 20a and out of the enteral feeding tube 12, 12a by way of gravity. Air molecules are introduced into the fluid chamber 28, 28a by way of the through hole 16, 16a to prevent formation of the vacuum in the fluid chamber 28, 28a that might prevent fluid flow through the enteral feeding tube 12, 12a. At certain times, particulate may clog the reduced size throat 20, 20a or the enteral feeding tube 12, 12a. This prevents flow of liquid nutrients 14, 14a to the infant. The infant is not capable of sucking the particulate out of the reduced size throat 20, 20a or the enteral feeding tube 12, 12a. As such, the clog must be cleared by intervention by an adult.

The clog may be cleared by increasing the pressure within the fluid chamber 28, 28a which correspondingly increases pressure within the liquid nutrient 14, 14a to urge the particulate out of the reduced size throat 20, 20a and the enteral feeding tube 12, 12a. The fluid chamber 28, 28a may be increased in pressure by way of an integrated pump shown in FIGS. 1 and 2 or by a separate external pump shown in FIG. 3.

Referring now to FIGS. 1 and 2, the pump may be integrally formed with the cover 30. To operate the pump, the operator or adult may seal off the through hole 16 with his/her finger. The operator places his/her finger on the through hole 16. The operator then applies pressure to the diaphragm 22 which forms an airtight seal such that air molecules cannot pass through the through hole 16. With the same motion, the adult continues to push downwardly on the diaphragm 22 to displace the air within the fluid chamber 28. This increases the pressure within the fluid chamber 28 as well as the liquid nutrients 14 to clear the clog within the system. When the adult removes his/her finger from the diaphragm 22, the convolutes 38 urge the diaphragm 22 back up to its normal upward position. When the infant feeding device 10 becomes clogged again, the user may close the through hole 16 and press downward to re-clear the system.

In the embodiment shown in FIG. 3, the aspiration bulb 24 is utilized to increase the pressure within the fluid chamber 28 for clearing the system. In particular, during use, when the reduced size throat 20a or the enteral feeding tube 12a is clogged, the operator engages the tapered stem 56 of the aspiration bulb 24 to the inner periphery 58 of the through hole 16a. This forms an airtight seal such that upon depression of the bulb portion 60 of the aspiration bulb 24, the gas pressure of the fluid chamber 28a increases thereby increasing the pressure within the liquid nutrients 14a and urging particulates clogging the reduced size throat 20a and the enteral feeding tube 12a out of the system. Any further clogging of the system may be cleared by re-pumping the fluid chamber 28a with the aspiration bulb 24.

The infant feeding device 10, 10a provides for an easy and convenient method of clearing clogs within the system. In the embodiment shown in FIGS. 1 and 2, a person's finger seals the through hole 16 and also actuates the pumping action. This is accomplished in one single motion. Similarly, with respect to the embodiment shown in FIG. 3, the aspiration bulb 24 seals the through hole 16a and also pumps or increases air pressure within the fluid chamber 28a of the gravity feeding container 26a. This provides for a one hand operation for both the sealing and pumping action. This allows the medical professional or adult to utilize his/her other hand for other purposes. Additionally, the hydrophobic filter 46, 46a prevents spillage of liquid nutrients 14 when the infant feeding device 10, 10a is accidentally dropped or otherwise inverted. Additionally, contaminants are less likely to be introduced into the fluid chamber 28 since the hydrophobic filter 46 prevents passage of liquid.

Figure 4:
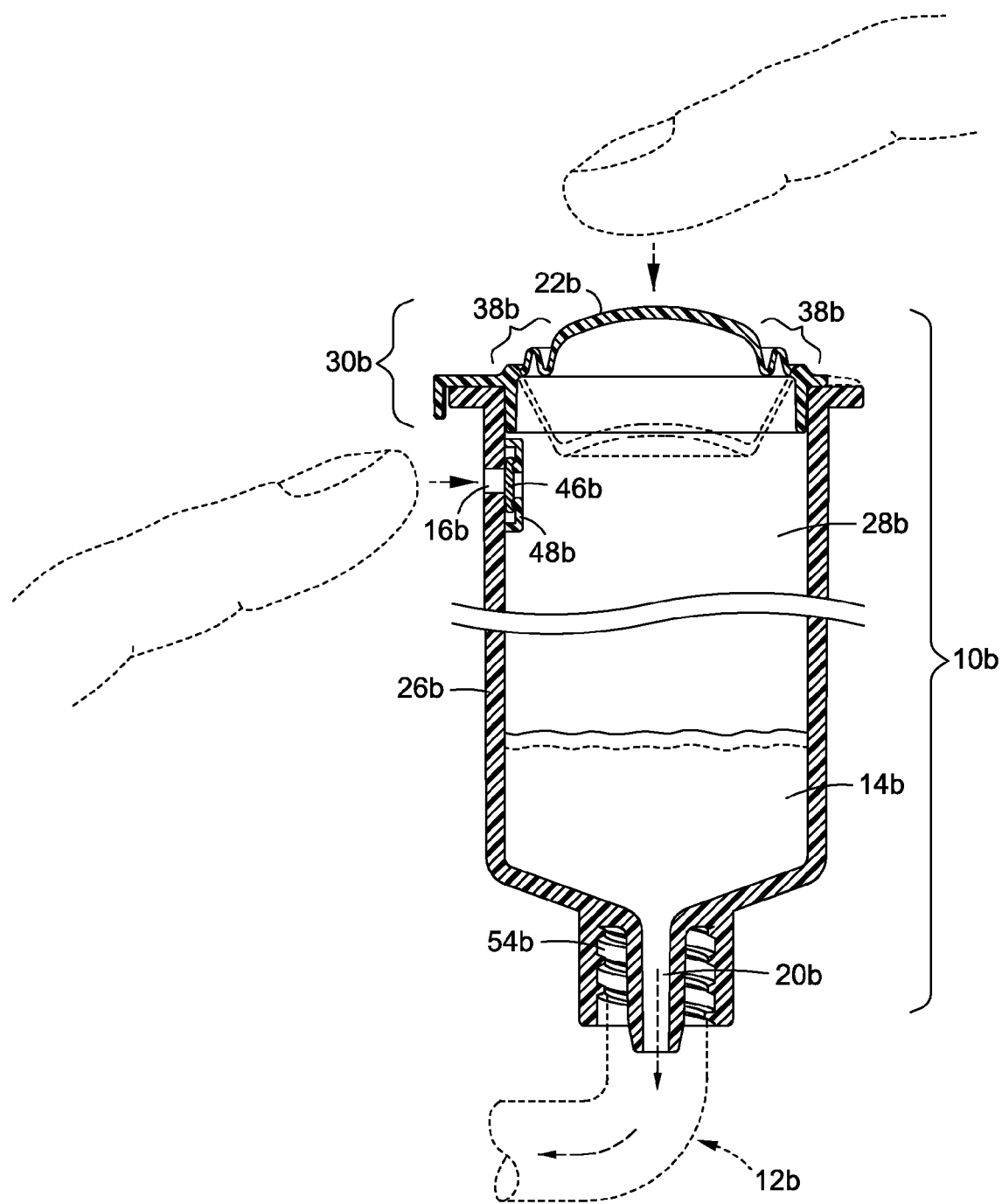
FIG. 4 is a cross sectional view of a third embodiment of an infant feeding device.

Referring now to FIG. 4, an alternate embodiment is shown. The infant feeding device 10b is similar to the infant feeding device 10 shown in FIGS. 1 and 2. The infant feeding device 10b may have a cover 30b. Instead of the cover 30b having through holes 16, 16a, the side wall of the gravity feeding container 26b has a through hole 16b. During use, as the liquid nutrients 14b are being fed out of the reduced size throat 20b and the enteral feeding tube 12b, air molecules are introduced into the fluid chamber 28b by way of the through holes 16b. This prevents formation of a vacuum within the fluid chamber 28b such that gravity is allowed to flow the liquid nutrients 14b out of the enteral feeding tube 12b. A hydrophobic filter 46b may be disposed over the through hole 16b and retained by the retainer 48b. The hydrophobic filter 46b allows air molecules to enter the fluid chamber 28b to prevent formation of the vacuum discussed above. Also, the hydrophobic filter 46b prevents liquid nutrients 14b from spilling out of the infant feeding device 10b out of the through hole 16b during accidental dropping or inversion of the infant feeding device 10b. During use, the reduced size throat 20b or the enteral feeding tube 12b may be clogged. To clear the clog, the user plugs the through hole 16b such as by placing his/her finger over the through hole 16b. The user then depresses the diaphragm 22b downward to increase air pressure within the fluid chamber 28b. This increases the pressure within the reduced size throat 20b and the enteral feeding tube 12b to clear any clogs within the system. After the clog is cleared, the user releases the diaphragm 22b which springs back upward to its normal position and removes his/her finger from the through hole 16b. The convolutes 38b allow the diaphragm 22b to be pushed downward and spring back upward to its normal position. The embodiment shown in FIG. 4 is a two finger or a two handed operation. For example, the thumb of the operator can seal the throughhole 16b while the index finger of the operator pushes the diaphragm 22b.

The devices 10, 10*a*, 10*b* may be held in the upright position as shown in FIGS. 1-4. The upright position is wherein the throughhole 16, 16*a*, 16*b* is positioned above the receptacle 54, 54*a*, 54*b*.

The above description is given by way of example, and not limitation. Given the above disclosure, one skilled in the art could devise variations that are within the scope and spirit of the invention disclosed herein, including various ways of molding the device 10, 10*a*. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A method of operating a feeding device for an infant, the method comprising the steps of:
   providing an enteral feeding tube to an infant;
   filling a rigid body defining a fluid chamber of the infant feeding device with liquid nutrients;
   orienting a reduced size throat of the infant feeding device to a lowered position to discharge the liquid nutrients from the fluid chamber by way of gravity;
   discharging the liquid nutrients out of the reduced size throat and through the enteral feeding tube to the infant by way of gravity by providing air communication between the fluid chamber and the environment through a vent formed above a liquid level of the liquid nutrients disposed within the fluid chamber;
   when the reduced size throat is clogged, placing a user's finger in direct contact with the vent to close the vent and increasing pressure within the fluid chamber to unclog the reduced size throat by pushing the closed vent toward the fluid chamber to increase pressure within the fluid chamber;
   removing the user's finger from the vent to open the vent; and resuming the discharging step.

2. The method of claim 1 wherein the vent is traverseable between a depressed position and a retracted position, and the pushing step comprises the step of pushing the vent located within a diaphragm toward the fluid chamber.

* * * * *